United States Patent
Nakamura et al.

(10) Patent No.: US 11,547,984 B2
(45) Date of Patent: Jan. 10, 2023

(54) PRODUCTION METHODS OF CATALYST FOR HYDROGENATION AND DIOL

(71) Applicant: Toyo Tire Corporation, Itami (JP)

(72) Inventors: Norihiko Nakamura, Itami (JP); Keiichi Tomishige, Sendai (JP); Yoshinao Nakagawa, Sendai (JP); Masazumi Tamura, Sendai (JP)

(73) Assignee: TOYO TIRE CORPORATION, Itami (JP)

( * ) Notice: Subject to any disclaimer, the term of this patent is extended or adjusted under 35 U.S.C. 154(b) by 141 days.

(21) Appl. No.: 17/057,985

(22) PCT Filed: Jul. 6, 2018

(86) PCT No.: PCT/JP2018/025669
§ 371 (c)(1),
(2) Date: Nov. 23, 2020

(87) PCT Pub. No.: WO2020/008617
PCT Pub. Date: Jan. 9, 2020

(65) Prior Publication Data
US 2021/0205792 A1    Jul. 8, 2021

(51) Int. Cl.
B01J 23/652    (2006.01)
B01J 23/89    (2006.01)
B01J 37/16    (2006.01)
C07C 29/149    (2006.01)
C07C 31/20    (2006.01)

(52) U.S. Cl.
CPC ....... B01J 23/6525 (2013.01); B01J 23/8913 (2013.01); B01J 37/16 (2013.01); C07C 29/149 (2013.01); C07C 31/20 (2013.01)

(58) Field of Classification Search
CPC .... B01J 23/6525; B01J 23/8913; B01J 37/16; C07C 29/149; C07C 31/20
USPC ........................................ 502/313, 326, 339
See application file for complete search history.

(56) References Cited

U.S. PATENT DOCUMENTS

| | | | | |
|---|---|---|---|---|
| 4,777,303 A * | 10/1988 | Kitson | ................ | C07C 29/149 |
| | | | | 502/313 |
| 4,985,572 A * | 1/1991 | Kitson | ................ | C07C 29/177 |
| | | | | 568/885 |
| 5,149,680 A * | 9/1992 | Kitson | ................ | B01J 23/688 |
| | | | | 502/313 |
| 6,486,367 B1 * | 11/2002 | Budge | ................ | C07C 29/177 |
| | | | | 568/864 |
| 6,906,228 B2 * | 6/2005 | Fischer | ................ | B01J 21/18 |
| | | | | 568/876 |
| 2001/0029302 A1 | 10/2001 | Cho et al. | | |
| 2010/0029996 A1 * | 2/2010 | Danjo | ................ | B01J 23/894 |
| | | | | 502/313 |
| 2016/0200646 A1 | 7/2016 | Murphy et al. | | |

FOREIGN PATENT DOCUMENTS

| | | | | |
|---|---|---|---|---|
| CA | 2311589 A1 * | 6/1999 | ........... | C07C 29/149 |
| CN | 104722321 A | 6/2015 | | |
| JP | 6-501875 A | 3/1994 | | |
| JP | 6-145159 A | 5/1994 | | |
| JP | 7-82190 A | 3/1995 | | |
| JP | 7-118187 A | 5/1995 | | |
| JP | 2001-2604 A | 1/2001 | | |
| JP | 2001-46871 A | 2/2001 | | |
| JP | 2001-46873 A | 2/2001 | | |
| JP | 2015-74619 A | 4/2015 | | |
| JP | 2016-532704 A | 10/2016 | | |
| WO | 92/02298 A1 | 2/1992 | | |

OTHER PUBLICATIONS

English translation of the Written Opinion for PCT/JP2018/025669, (dated 2018).*
International Search Report dated Sep. 25, 2018, issued in counterpart International Application No. PCT/JP2018/025669. (2 pages).
Takeda et al., "Hydrogenation of dicarboxylic acids to diols over Re-Pd catalysts", Catalysis Science & Technology, (2016), 6, pp. 5668-5683. (16 pages).
Jeong et al., "The hydrogenation of maleic anhydride to Y-butyrolaction using mixed metal oxide catalysts in a batch-type reactor", Fuel Processing Technology, Feb. 4, 2006, vol. 87, pp. 497-503. ( 7 pages).
Office Action dated Apr. 7, 2022, issued in counterpart JP Application No. 2020-528646, with English Translation. (8 pages).
Office Action dated Nov. 2, 2021, issued in counterpart JP Application No. 2020-528646, with English Translation. (8 pages).

* cited by examiner

*Primary Examiner* — Patricia L. Hailey
(74) *Attorney, Agent, or Firm* — WHDA, LLP

(57) ABSTRACT

The invention relates to a novel catalyst for hydrogenation for hydrogenating at least one of dicarboxylic acid or its acid anhydride. The catalyst for hydrogenation according to a first embodiment is obtained by supporting at least one of palladium or platinum, and cobalt on a carrier, and subjecting the resulting carrier to a reduction treatment at 400 K or higher. The catalyst for hydrogenation according to a second embodiment is obtained by supporting at least one of palladium or platinum, and molybdenum on a carrier, and subjecting the resulting carrier to a reduction treatment at 500 K or higher.

16 Claims, No Drawings

PRODUCTION METHODS OF CATALYST FOR HYDROGENATION AND DIOL

TECHNICAL FIELD

An embodiment of the present invention relates to a production method of a catalyst for hydrogenation for hydrogenating at least one of dicarboxylic acid or its acid anhydride. Furthermore, it relates to a production method of a diol using the catalyst for hydrogenation.

BACKGROUND ART

Diol is a useful substance as a raw material of a polyester resin, a polyurethane resin, an adhesive and the like. A method for hydrogenating dicarboxylic acid such as succinic acid or maleic acid in the presence of a catalyst is known as a method for producing 1,4-butanediol as one kind of a diol.

Conventionally, a catalyst comprising a carrier such as silica having palladium and rhenium supported thereon (for example, Re—Pd/SiO$_2$) is generally used as such a catalyst for hydrogenation (see Patent Literature 1 and Non-Patent literature 1). However, the Re—Pd/SiO$_2$ catalyst is expensive, and for this reason, the development of more inexpensive alternative catalyst is desired.

As the catalyst for hydrogenation of this kind, Patent Literature 2 discloses a catalyst comprising a carrier having supported thereon at least one metal selected from rhenium, molybdenum, palladium, silver and nickel, together with ruthenium and tin. Furthermore, Patent Literature 3 discloses a catalyst containing at least two of 21 metals including rhodium, iridium, platinum, palladium and molybdenum, and a metal of Group 5, 6 or 7 in the periodic table. However, a catalyst comprising a carrier having supported thereon palladium and/or platinum, and molybdenum and/or cobalt is not disclosed.

On the other hand, Non-Patent Literature 1 describes a catalyst obtained by reducing Mo—Pd/SiO$_2$ comprising silica having supported thereon palladium and molybdenum at 413 K in a liquid phase, but describes that this catalyst does not have catalytic activity to a hydrogenation reaction of succinic acid.

CITATION LIST

Patent Literature

Patent Literature 1: JP-A-7-82190
Patent Literature 2: JP-A-2001-2604
Patent Literature 3: JP-A-2015-74619

Non-Patent Literature

Non-Patent Literature 1: Yasuyuki Takeda and four others, "Hydrogenation of dicarboxylic acids to diols over Re—Pd catalysts", Catalysis Science & Technology, 2016, 6, pp 5668-5683

SUMMARY OF INVENTION

Technical Problem

An embodiment of the present invention has an object to provide a novel catalyst for hydrogenation for hydrogenating at least one of dicarboxylic acid or its acid anhydride.

Solution to Problem

The embodiment of the present invention includes the following aspects.

[1] A production method of a catalyst for hydrogenation for hydrogenating at least one of dicarboxylic acid or its acid anhydride, including supporting at least one of palladium or platinum, and cobalt on a carrier, and subjecting the resulting carrier to a reduction treatment, at 400 K or higher.

[2] A production method of a catalyst for hydrogenation for hydrogenating at least one of dicarboxylic acid or its acid anhydride, including supporting at least one of palladium or platinum, and molybdenum on a carrier, and subjecting the resulting carrier to a reduction treatment at 500 K or higher.

[3] A production method of a diol, including subjecting a carrier having supported thereon at least one of palladium or platinum, and cobalt to a reduction treatment at 400 K or higher, and hydrogenating at least one of dicarboxylic acid or its acid anhydride in the presence of the reduced carrier as a catalyst, thereby producing a diol.

[4] A production method of a diol, including subjecting a carrier having supported thereon at least one of palladium or platinum, and molybdenum to a reduction treatment at 500 K or higher, and hydrogenating at least one of dicarboxylic acid or its acid anhydride in the presence of the reduced carrier as a catalyst, thereby producing a diol.

[5] A catalyst for hydrogenation for hydrogenating at least one of dicarboxylic acid or its acid anhydride, which contains a carrier, at least one of palladium or platinum supported on the carrier, and cobalt supported on the carrier, and is obtained by subjecting the resulting carrier to a reduction treatment at 400 K or higher.

[6] A catalyst for hydrogenation for hydrogenating at least one of dicarboxylic acid or its acid anhydride, which contains a carrier, at least one of palladium or platinum supported on the carrier, and molybdenum supported on the carrier, and is obtained by subjecting the resulting carrier to a reduction treatment at 500 K or higher.

Advantageous Effects of Invention

According to the embodiment of the present invention, a novel catalyst for hydrogenation that can hydrogenate dicarboxylic acid and/or a dicarboxylic anhydride can be provided.

MODE FOR CARRYING OUT INVENTION

The catalyst for hydrogenation (hereinafter simply referred to as a "catalyst") according to the present embodiment is a catalyst for hydrogenating at least one of dicarboxylic acid or its acid anhydride (hereinafter referred to as "dicarboxylic acids"), and contains a carrier, a first metal and a second metal.

Here, the first metal is at least one of palladium or platinum (that is, palladium and/or platinum). The second metal is cobalt in the catalyst for hydrogenation according to a first embodiment (hereinafter referred to as "catalyst-1") and is molybdenum in the catalyst for hydrogenation according to a second embodiment (hereinafter referred to as "catalyst-2"). The embodiments do not exclude combined use of cobalt and molybdenum.

The carrier includes conventional carriers that are generally used as carriers of various catalysts, and is not particularly limited. Examples of the carrier include inorganic carriers such as inorganic oxide and activated carbon, and organic carriers such as ion exchanged resin. In one embodiment, from the standpoint of excellent catalytic activity, as the carrier, inorganic oxide and/or activated carbon are preferably used and inorganic oxide is more preferably used.

Examples of the inorganic oxide include silica ($SiO_2$), titania ($TiO_2$), zirconia ($ZrO_2$), alumina ($Al_2O_3$), magnesia (MgO) and a composite of two or more of those inorganic oxides (for example, zeolite). Those may be used in one kind alone and may be used by combining two or more kinds. In one embodiment, at least one selected from the group consisting of silica, titania and alumina may be used as the carrier.

Specific surface area of the carrier is not particularly limited, but is preferably 50 $m^2/g$ or more from the standpoint that a metal can be arranged in high dispersion or its aggregation is suppressed. For example, the specific surface area may be 50 to 1500 $m^2/g$ and may be 100 to 1000 $m^2/g$. The specific surface area is a nitrogen adsorption specific surface area measured according to BET method.

In the catalyst described above, the first metal and the second metal are supported on the carrier. The form of those first metal and second metal is not particularly limited. Those metals may be, for example, an elemental metal and may be the form of a compound containing a metal, such as a salt, an oxide, a hydroxide or a complex. The elemental metal means a substance in a metal state having an oxidation number of 0, and is hereinafter sometimes called a "simple substance". In one embodiment, the catalyst may contain a simple substance of the first metal and an oxide of the second metal, and in this case, the second metal may contain a substance in the form of a simple substance by the reduction of a part of an oxide. Furthermore, in other embodiment, the catalyst may contain a simple substance of the first metal, and a simple substance of the second metal. In other words, the catalyst may contain a simple substance of the first metal, and a simple substance and/or an oxide of the second metal.

The first metal and the second metal may be directly supported on the carrier and may be indirectly supported thereon. For example, the first metal may be directly supported on the carrier and may be supported on the carrier through the second metal, and those may be mixed. Furthermore, the second metal may be directly supported on the carrier and may be supported on the carrier through the first metal, and those may be mixed.

When plural kinds of carriers are used, the first metal and the second metal may be supported on the same carrier and may be supported on separate carriers. Preferably, the first metal and second metal are supported on the same carrier.

The amount of the first metal supported on the carrier is not particularly limited, but is preferably 0.01 to 50% by mass, more preferably 0.01 to 20% by mass, still more preferably 0.5 to 15% by mass, and particularly preferably 1.0 to 10% by weight, in terms of the metal, based on the mass of the entire catalyst. When the amount of the first metal supported is 0.01% by mass or more, the conversion rate of the dicarboxylic acid tends to be further improved. On the other hand, when the amount of the first metal supported is 50% by mass or less, economical advantage tends to be obtained.

The amount of the second metal supported on the carrier is not particularly limited, but from the standpoint of the conversion rate of the dicarboxylic acid, the second meal/first metal is preferably 50/1 to 1/1, more preferably 32/1 to 8/1, and still more preferably 32/1 to 12/1, in terms of a molar ratio (metal conversion) to the first metal. The molar ratio may be 25/1 to 15/1.

The catalyst for hydrogenation according to the present embodiment may further contain a metal other than the first metal and the second metal, for example, an active metal for hydrogenation such as rhodium, iridium, ruthenium, gold, silver, copper or nickel, as a metal component.

The average particle diameter of the catalyst for hydrogenation according to the present embodiment is not particularly limited, and, for example, may be 50 to 200 μm and may be 75 to 150 μm. Furthermore, the shape of the catalyst is not particularly limited, and examples of the shape include a powdery shape, a granular shape and a molded article shape.

The catalyst-1 according to the first embodiment may contain palladium and cobalt. In this case, the catalyst-1 may contain a simple substance of palladium and an oxide of cobalt (a part of an oxide is reduced and a substance in the state of a simple substance may be contained) and may contain a simple substance of palladium and a simple substance of cobalt.

The catalyst-2 according to the second embodiment may contain palladium and molybdenum. In this case, the catalyst-2 may contain a simple substance of palladium and an oxide of molybdenum (a part of an oxide is reduced and a substance in the state of a simple substance may be contained) and may contain a simple substance of palladium and a simple substance of molybdenum.

In producing the catalyst for hydrogenation according to the present embodiment, a method of supporting the first metal and the second metal on the carrier and subjecting the resulting carrier to a reduction treatment at a predetermined temperature or higher can be used.

The method for supporting the first metal and the second metal on the carrier is not particularly limited, and the conventional methods can be used. For example, a raw material compound of a metal component to be supported is dissolved in a solvent such as water to prepare a solution of a metal compound, and the carrier is immersed with this solution, followed by drying and baking, thereby the metal component can be supported on the carrier.

The order of supporting each metal component on the carrier is not particularly limited, and all the metals may be simultaneously supported or each component may be individually supported. For example, a method of impregnating a carrier with a solution containing the first metal, drying the carrier, impregnating the carrier with a solution containing the second metal, drying the carrier, and the baking the carrier is exemplified.

As a raw material compound of the metal component that is used in the catalyst preparation, a mineral acid salt such as a nitrate, a sulfate or a hydrochloride, an organic acid salt such as an acetate, a hydroxide, an oxide, an organometal compound, and the like can be generally used, although depending on the preparation method of the catalyst. Of those, a water-soluble raw material compound is preferred. Specifically, examples of the raw material compound of palladium include palladium chloride, palladium nitrate, palladium sulfate, palladium acetate and dinitrodiamine palladium. Examples of the raw material compound of platinum include chloroplatinic acid, sodium chloroplatinate, platinum acetyl acetonate, dinitrodiamine platinum and tetraamine platinum nitrate. Examples of the raw material compound of molybdenum include hexaammonium heptamolybdate tetrahydrate and molybdenum chloride. Examples of the raw material compound of cobalt, include cobalt dichloride, cobalt dibromide, cobalt difluoride, cobalt nitrate and cobalt acetate. Those may be used in one kind alone and may be used by combining two or more kinds.

The drying after impregnating the carrier with a solution containing the metal component can be conducted by, for example, heating the carrier at a temperature of 330 to 470

K under a reduced pressure, as necessary. Furthermore, the baking after drying can be conducted, for example, at a temperature of 373 to 873 K while flowing nitrogen, air or the like.

In the present embodiment, the carrier having supported thereon the first metal and the second metal after baking is subjected to a reduction treatment at the predetermined temperature or higher. By conducting the reduction treatment at high temperature, the catalytic effect of hydrogenating dicarboxylic acids and forming a diol can be enhanced. The structure of the catalyst changes by the reduction temperature, and oxidation and reduction state of the metal supported changes. It is considered that as the reduction temperature is high, the state that the second metal has been oxidized changes to the state that the second metal has been reduced, and the catalytic activity is improved by the synergistic effect between metals.

In producing the catalyst-1 according to the first embodiment, the reduction temperature is 400 K or higher. In other words, the carrier having the first metal and cobalt supported thereon is subjected to the reduction treatment at 400 K or higher. The reduction temperature in this case is preferably 500 K or higher and more preferably 550 K or higher. The upper limit of the reduction temperature is not particularly limited. For example, the upper limit may be 1500 K or lower and may be 1300 K or lower. In one embodiment, in the case of the carrier having palladium and cobalt supported thereon, the reduction temperature is preferably 400 to 1200 K and more preferably 500 to 1000 K. The reduction temperature may be 550 to 800 K.

In the case of producing the catalyst-2 according to the second embodiment, the reduction temperature is 500 K or higher. In other words, the carrier having the first metal and molybdenum supported thereon is subjected to a reduction treatment at 500 K or higher. The reduction temperature in this case is preferably 550 K or higher and more preferably 850 K or higher. The upper limit of the reduction temperature is not particularly limited. For example, the upper limit may be 1500 K or lower and may be 1300 K or lower. In one embodiment, in the case of the carrier having palladium and molybdenum supported thereon, the reduction temperature is preferably 650 to 1400 K, more preferably 800 to 1300 K and still more preferably 1000 to 1200 K.

The reduction treatment may be any of gas phase reduction and liquid phase reduction, but is preferably gas phase reduction that conducts the reduction treatment in a gas phase. The gas phase reduction can be conducted by contacting the carrier with a reducing gas in a gas phase. As the reducing gas, hydrogen, hydrazine vapor, formalin, carbon monoxide or the like can be used. For example, the baked carrier is placed in a vessel and heated to a desired temperature. Thereafter, the reduction may be performed by filling the vessel with a reducing gas or the reduction may be conducted by flowing a reducing gas through the vessel.

The catalyst for hydrogenation according to the present embodiment can be used for hydrogenating dicarboxylic acids. The catalyst is preferably used as a catalyst for producing a diol from dicarboxylic acids. The production method of a diol according to the preferred embodiment is described below.

The production method of a diol according to the embodiment is to produce a diol by subjecting a carrier having the first metal and the second metal supported thereon to the reduction treatment at the predetermined temperature or higher as described above, and then hydrogenating dicarboxylic acids in the presence of the reduced carrier as a catalyst.

The reduction temperature in the reduction treatment is as described above. When the second metal is cobalt (in the case of the catalyst-1), the reduction temperature is 400 K or higher, and when the second metal is molybdenum (in the case of the catalyst-2), the reduction temperature is 500 K or higher. The preferred reduction temperature in both the catalyst-1 and the catalyst-2 is as described above. The catalyst after the reduction treatment is that oxidation and reduction state of a metal is easy to change. Therefore, the catalyst is preferably immediately subjected to a hydrogenation reaction after the reduction treatment.

The hydrogenation reaction is to produce a corresponding diol by contacting dicarboxylic acids with the reduced catalyst and a hydrogen source.

Examples of dicarboxylic acids include aliphatic saturated dicarboxylic acids such as oxalic acid, malonic acid, succinic acid, glutaric acid, adipic acid, pimelic acid, suberic acid, azelaic acid, sebacic acid and methylsuccinic acid, and their acid anhydrides. Examples of dicarboxylic acids further include aliphatic unsaturated dicarboxylic acids such as fumaric acid, maleic acid, glutaconic acid and citraconic acid, and their acid anhydrides. Those may be used in one kind alone and may be used by combining two or more kinds. Of those, at least one selected from the group consisting of succinic acid, succinic anhydride, maleic acid and maleic anhydride is preferably used as the dicarboxylic acids.

The hydrogen source is not particularly limited so long as it is a compound that provides hydrogen. Examples of the hydrogen source include a reducing gas such as a hydrogen gas or an ammonia gas (the reducing gas may be diluted with an inert gas such as nitrogen, helium or argon), water, an alcohol and formic acid. A reducing gas is preferably used and a hydrogen gas is more preferably used. The amount of the hydrogen source is not particularly limited. For example, the amount may be 5 to 200 moles and may be 10 to 160 moles, based on 1 mole of the dicarboxylic acids.

The amount of the catalyst is not particularly limited. For example, the amount may be 0.0005 to 0.1 mole and may be 0.001 to 0.075 mole, in terms of the metal atom supported, based on 1 mole of the dicarboxylic acids.

The hydrogenation reaction is preferably conducted in a solvent. The solvent used is not particularly limited so long as it does not impair the reaction. Examples of the solvent include water; an alcohol such as methanol, ethanol, isopropyl alcohol or n-butyl alcohol; a hydrocarbon such as heptane, hexane, cyclohexane or toluene; an amides such as N,N-dimethylformamide or N,N-dimethylacetamide; ethers such as diethyl ether, diisopropyl ether, 1,2-dimethoxymethane, diethylene glycol dimethyl ether, tetrahydrofuran or 1,4-dioxane; and halogenated hydrocarbons such as methylene chloride, dichloroethane or chlorocyclohexane. Of those, water, hydrocarbons and ethers are preferred, and water and ethers are more preferred. Those solvents may be used in one kind alone and may be used by mixing two or more kinds. The amount of the solvent used is not particularly limited. For example, the amount may be 0.05 to 100 g and may be 1 to 30 g, based on 1 g of the dicarboxylic acids.

The hydrogenation reaction is conducted by a method of, for example, mixing the dicarboxylic acids, the catalyst and the solvent, and reacting those in the presence of the hydrogen source while stirring. The reaction temperature is not particularly limited. For example, the reaction temperature may be 300 to 600 K and may be 400 to 500 K. The reaction pressure is not particularly limited. For example, the reaction pressure may be ordinary pressure to 20 MPa, may be 3 to 15 MPa, and may be 5 to 10 MPa, as a hydrogen partial pressure. The reaction time is not particularly limited. For example, the reaction time may be 1 to 120 hours, may be 4 to 120 hours, may be 10 to 100 hours and may be 20 to 80 hours.

The reaction form of the hydrogenation reaction can select any method of a batchwise type and a continuous type, depending on the form of the catalyst. Furthermore, the hydrogenation reaction can be carried out in any reaction system of a homogeneous system and a heterogenous system (suspension reaction), depending on the properties of the catalyst.

The diol obtained by the production method of a diol according to the present embodiment is a diol corresponding to the dicarboxylic acids as a raw material, and a diol in which two carboxyl groups of the dicarboxylic acids are replaced by hydroxyl groups is obtained. When an unsaturated dicarboxylic acid is used as the raw material, a carbon-carbon double bond is hydrogenated by the hydrogenation reaction, and a saturated diol is obtained.

For example, when at least one selected from the group consisting of succinic acid, succinic anhydride, maleic acid and maleic anhydride is selected as the dicarboxylic acid and is used as a substrate, those are converted to 1,4-butanediol through γ-butyrolactone as an intermediate. Therefore, the above catalyst can be utilized in the production of 1,4-butanediol.

The diol obtained can be used as, for example, a raw material of a polyester resin, a polyurethane resin or an adhesive.

EXAMPLES

Examples are described below, but the present invention is not construed as being limited to those examples.

Production Example 1 Preparation of Mo—Pd Catalyst ($MoO_x$—$Pd/SiO_a$)

Silica ($SiO_2$) (manufactured by Fuji Silysia Chemical Ltd., product name "CARiACT G-6", specific surface area: 485 $m^2/g$, pore volume: 0.74 mL/g, packing density: 0.49 g/mL, water content: 0.2% by mass, average particle diameter: 75 to 150 μm, pretreatment: 973 K, 1 hour) was used as a carrier.

0.43 g of a palladium nitrate ($Pd(NO_3)_2$) solution (manufactured by Wako Pure Chemical Industries Ltd., 10% by mass Pd ($NO_3)_2$) was put in a 5 mL sample bottle, and diluted with distilled water to obtain 5 g of a solution. 1.6 g of the silica was put in a 100 mL beaker, 5 g of the diluted palladium nitrate solution was added to the beaker little by little while heating to 353 to 363 K with a hot stirrer, and Pd was supported on the silica based on an incipient-wetness method while sufficiently mixing. After vaporizing water on the stirrer, the silica having palladium supported thereon was dried in an oven at 383 K overnight.

0.664 g of hexaammonium heptamolybdate tetrahydrate (($NH_4)_6Mo_7O_{24} \cdot 4H_2O$, manufactured by Wako Pure Chemical industries Ltd., 99.0%) was put in a small bottle, and distilled water was added to the small bottle to prepare 5 g of an aqueous solution. 5 g of the hexaammonium heptamolybdate tetrahydrate solution prepared was added to the beaker containing therein the silica having palladium supported thereon little by little while heating the beaker to 353 to 363 K by a hot stirrer, and the supporting based on an incipient-wetness method was repeatedly conducted until a molar ratio of molybdenum to palladium became Mo/Pd=20. After vaporizing water on the stirrer, the silica having palladium and molybdenum supported thereon was dried in an oven at 383 K overnight. Thereafter, the carrier obtained was placed in a muffle furnace, heated to 673 K in a temperature rising rate of 10 K/min, and then baked at 673 K for 3 hours (temperature rising rate: 10 K/min). Thus, Mo—Pd catalyst ($MoO_x$—$Pd/SiO_2$) was obtained (the amount of palladium supported is 1.0% by mass in terms of metal, based on the mass of the entire catalyst. Mo/Pd=20/1 (molar ratio)). $MoO_x$ may contain a compound of x=0 (that is, a simple substance of the oxidation number of 0).

Production Example 2 Preparation of Co—Pd Catalyst ($CoO_x$—$Pd/SiO_2$)

0.43 g of a palladium nitrate ($Pd(NO_3)_2$) solution (manufactured by Wako Pure Chemical Industries Ltd., 10% by mass Pd ($NO_3)_2$) was put in a 5 mL sample bottle, and diluted with distilled water to obtain 5 g of a solution. 1.7 g of silica ($SiO_2$) (manufactured by Fuji Silysia Chemical Ltd., product, name "CARiACT G-6") was put in a 100 mL beaker, 5 g of the diluted palladium nitrate solution was added to the beaker little by little while heating to 353 to 363 K with a hot stirrer, and Pd was supported on the silica based on an incipient-wetness method while sufficiently mixing. After vaporizing water on the stirrer, the silica having palladium supported thereon vas dried in an oven at 383 K overnight.

1.09 g of cobalt nitrate (($Co(NO_3)_2 \cdot 6H_2O$, manufactured by Wako Pure Chemical Industries Ltd., 98.0%) was put in a small bottle, and distilled water was added to the small bottle to prepare 5 g of an aqueous solution. 5 g of the hexaammonium heptamolybdate tetrahydrate solution prepared was added to the beaker containing therein the silica having palladium supported thereon little by little while heating the beaker to 353 to 363 K by a hot stirrer, and the supporting based on an incipient-wetness method was repeatedly conducted until a molar ratio of cobalt to palladium became Co/Pd=20. After vaporizing water on the stirrer, the silica having palladium and cobalt supported thereon was dried in an oven at 383 K overnight. Thereafter, the carrier obtained was placed in a muffle furnace, heated to 673 K in a temperature rising rate of 10 K/min, and then baked at 673 K for 3 hours. Thus, Co—Pd catalyst ($CoO_x$—$Pd/SiO_2$) was obtained (the amount of palladium supported is 1.0% by mass in terms of metal, based on the mass of the entire catalyst. Co/Pd=20/1 (molar ratio)). $CoO_x$ may contain a compound of x=0 (that is, a simple substance of the oxidation number of 0).

Production Example 3 Preparation of Mo Catalyst ($MoO_x/SiO_2$)

0.66 g of hexaammonium heptamolybdate tetrahydrate (($NH_4)_6Mo_7O_{24} \cdot 4H_2O$, manufactured by Wako Pure Chemical Industries Ltd., 99.0%) was put in a 5 mL sample bottle, and distilled water was added to the small bottle to prepare 5 g of an aqueous solution. 1.64 g of silica ($SiO_2$) (manufactured by Fuji Silysia Chemical Ltd., product name "CARiACT G-6") was put in a 100 mL beaker, 5 g of the hexaammonium heptamolybdate tetrahydrate solution was added to the beaker little by little while heating to 353 to 363 K with a hot stirrer, and the supporting was conducted based on an incipient-wetness method while sufficiently mixing. After vaporizing water on the stirrer, the silica having molybdenum supported thereon was dried in an oven at 383 K overnight. Thereafter, the carrier obtained was placed in a muffle furnace, heated to 673K in a temperature rising rate of 10 K/min, and then baked at 673 K for 3 hours. Thus, Mo catalyst ($MoO_x/SiO_2$) was obtained (the amount of molybdenum supported is 18% by mass in terms of metal, based on the mass of the entire catalyst).

Production Example 4 Preparation of Pd Catalyst ($Pd/SiO_2$)

0.43 g of palladium nitrate ($Pd(NO_3)_2$) solution (manufactured by Wako Pure Chemical Industries Ltd., 10% by mass $Pd(NO_3)_2$) was put in a 5 mL sample bottle, and diluted with distilled water to obtain 5 g of a solution. 1.98 g of silica ($SiO_2$) (manufactured by Fuji Silysia Chemical Ltd., product name "CARiACT G-6") was put in a 100 mL beaker, 5 g of the diluted palladium nitrate solution was added to the beaker little by little while heating to 353 to 363 K by a hot stirrer, and the supporting was conducted based or an incipient-wetness method while sufficiently stirring. After vaporizing water on the stirrer, the carrier obtained was dried in an oven at 383 K overnight. Thereafter, the carrier obtained was placed in a muffle furnace, heated to 673 K in a temperature rising rate of 10 K/min, and then baked at 673 K for 3 hours. Thus, Pd catalyst ($Pd/SiO_2$) was obtained (the amount of palladium supported is 1.0% by mass in terms of metal, based on the mass of the entire catalyst).

Production Example 5 Preparation of Co—Pd Catalyst ($CoO_x$—$Pd/SiO_2$)

Four Co—Pd catalysts ($CoO_x$—$Pd/SiO_2$) having different molar ratio were obtained in the same manner as Production Example 2, except for changing the molar ratio of cobalt to palladium to Co/Pd=8, 12, 16 and 32 (the amount of palladium supported is 1.0% by mass in terms of metal, based on the mass of the entire catalyst. Co/Pd=8, 12, 16 and 32 (molar ratio)).

Example 1

0.2 g of the Mo—Pd catalyst ($MoO_x$—$Pd/SiO_2$) obtained in Production Example 1 was placed in a quartz glass reaction tube (inner diameter 4 mm, outer diameter 6 mm, length 35 cm), and the reaction tube was set to a reduction apparatus. After nitrogen substitution, the reaction tube was heated to 673 K in a temperature rising rate of 10 K/min, and gas phase reduction was performed under the conditions of reduction temperature: 673 K and reduction time: 1 hour under hydrogen flowing, followed by cooling.

In a nitrogen-substituted glove box, 0.10 g of the Mo—Pd catalyst after reduction vas put in an autoclave (high pressure batch type reaction apparatus, volume: 190 mL) containing 1.0 g of succinic acid (manufactured by Wako Pure Chemical Industries Ltd., 99.5%) and 19 g of 1,4-dioxane (manufactured by Wako Pure Chemical Industries Ltd., 99.5%) as a solvent, and the autoclave was sealed. Hydrogen of 1 MPa was introduced in the autoclave, and the autoclave was heated to 473 K by a reactor. After the temperature rising, hydrogen of 8 MPa was introduced in the autoclave, and hydrogenation reaction was conducted in a stirring speed of 500 rpm for 4 hours. After completion of the reaction, the autoclave was cooled with a water bath, and a liquid phase and a gas phase were recovered. Regarding the recovered materials, the product was analyzed by the analysis method described hereinafter.

Examples 2 to 5 and Comparative Example 1

The gas phase reduction and hydrogenation reaction were conducted in the same manners as in Example 1, except that the reduction temperature in the gas phase reduction was changed to 873 K in Example 2, 1073 K in Example 3, 1173 K in Example 4, 1273 K in Example 5 and 473 K in Comparative Example 1, as shown in Table 1 below, and the products obtained were analyzed.

Example 6

0.2 g of the Co—Pd catalyst ($CoO_x$—$Pd/SiO_2$) obtained in Production Example 2 was placed in a quartz glass reaction tube (inner diameter 4 mm, outer diameter 6 mm, length 35 cm), and the reaction tube was set to a reduction apparatus. After nitrogen substitution, the reaction tube was heated to 473 k in a temperature rising rate of 10 K/min, and gas phase reduction was performed under the conditions of reduction temperature: 473 K and reduction time: 1 hour under hydrogen flowing, followed by cooling.

In a nitrogen-substituted glove box, 0.10 g of the Co—Pd catalyst after reduction vas put in an autoclave (high pressure batch type reaction apparatus, volume: 190 mL) containing 1.0 g of succinic acid (manufactured by Wako Pure Chemical Industries Ltd., 99.5%) and 19 g of 1,4-dioxane (manufactured by Wako Pure Chemical Industries Ltd., 99.5%) as a solvent, and the autoclave was sealed. Hydrogen of 1 MPa was introduced in the autoclave, and the autoclave was heated to 473 K by a reactor. After the temperature rising, hydrogen of 8 MPa was introduced in the autoclave, and hydrogenation reaction was conducted in a stirring speed of 500 rpm for 4 hours. After completion of the reaction, the autoclave was cooled with a water bath, and a liquid phase and a gas phase were recovered. Regarding the recovered materials, the product was analyzed in the same manner as in Example 1.

Examples 7 to 10

The gas phase reduction and the hydrogenation reaction were conducted in the same manner as in Example 6, except that the reduction temperature in the gas phase reduction was changed to 573 in Example 7, 673K in Example 8, 873 K in Example 9 and 1173 K in Example 10, as shown in Table 1 below. Products obtained were analyzed.

Comparative Example 2

0.2 g of the Mo catalyst ($MoO_x/SiO_2$) obtained in Production Example 3 was placed in a Quartz glass reaction tube (inner diameter 4 mm, outer diameter 6 mm, length 35 cm), and the reaction tube was set to a reduction apparatus. After nitrogen substitution, the reaction tube was heated to 1173 K in a temperature rising rate of 10 K/min, and gas phase reduction was performed under the conditions of reduction temperature: 1173 K and reduction time: 1 hour under hydrogen flowing, followed by cooling, using 0.10 of Mo catalyst after the reduction, the hydrogenation reaction of succinic acid was conducted in the same manner as in Example 1, and the product was analyzed.

Comparative Example 3

0.2 g of the Pd catalyst ($Pd/SiO_2$) obtained in Production Example 4 was placed in a quartz glass reaction tube (inner diameter 4 mm, outer diameter 6 mm, length 35 cm), and the reaction tube was set to a reduction apparatus. After nitrogen substitution, the reaction tube was heated to 1173 K in a temperature rising rate of 10 K/min, and gas phase reduction was performed under the conditions of reduction temperature: 1173 K and reduction time: 1 hour under hydrogen flowing, followed by cooling. Using 0.10 of Pd catalyst; after the reduction, the hydrogenation reaction of succinic acid was conducted in the same manner as in Example 1, and the product was analyzed.

The analytical conditions of the product are as follows. Using a gas chromatograph (GC) apparatus ("GC-2014" manufactured by Shimadzu Corporation), the liquid component was measured by "GC-FID", and the gas component was measured by "GC-FID with metanator". However, succinic acid has high boiling point, and is difficult to be measured with GC. Therefore, succinic acid was measured with HPLC ("LC-20AD" manufactured by Shimadzu Corporation).

Internal standard material: 2-Methoxyethanol 1.5 mL

The temperature of the column is constant as 333 K.
[(HPLC-RID (LC-20AD)]
Flow rate: 0.9000 mL/min, pressure: 6.0 MPa, column temperature: 323 K Regarding Examples 1 to 10 and Comparative Examples 1 to 3, conversion rate, selectivity and mass balance were calculated from the following formulae.

Conversion rate (%)=[Total carbon atoms (mol) of product/(Total carbon atoms (mol) of residual substrate+total carbon atoms (mol) of product)]×100

Selectivity (%) of each material=[Total carbon atoms (mol) of each material/Total carbon atoms (mol) of product]×100

Mass balance (%)=[(Total carbon atoms (mol) of residual substrate+total carbon atoms (mol) of product)/Total carbon atoms of substrate supplied]×100

TABLE 1

| | Catalyst | Reduction Temperature (K) | Conversion rate (%) | Selectivity (%) | | | | | | | | | | Mass Balance (%) |
| | | | | BDO | GBL | THF | BuA | BuOH | PrA | CO | $CO_2$ | $CH_4$ | $C_2H_6$ | |
|---|---|---|---|---|---|---|---|---|---|---|---|---|---|---|
| Com. Ex. 1 | $MoO_x$—Pd/$SiO_2$ | 473 | 6.4 | 0.0 | 82 | 18 | 0.0 | 0.0 | 0.0 | 0.2 | 0.0 | 0.0 | 0.0 | 103 |
| Ex. 1 | $MoO_x$—Pd/$SiO_2$ | 673 | 22 | 0.0 | 98 | 1.4 | 0.0 | 0.0 | 0.0 | 0.0 | 0.0 | 0.0 | 0.2 | 100 |
| Ex. 2 | $MoO_x$—Pd/$SiO_2$ | 873 | 50 | 0.2 | 96 | 3.1 | 0.3 | 0.1 | 0.2 | 0.0 | 0.0 | 0.0 | 0.1 | 95 |
| Ex. 3 | $MoO_x$—Pd/$SiO_2$ | 1073 | 64 | 2.0 | 96 | 1.8 | 0.1 | 0.1 | 0.2 | 0.0 | 0.0 | 0.0 | 0.0 | 97 |
| Ex. 4 | $MoO_x$—Pd/$SiO_2$ | 1173 | 65 | 3.2 | 95 | 1.5 | 0.1 | 0.1 | 0.1 | 0.0 | 0.0 | 0.0 | 0.0 | 96 |
| Ex. 5 | $MoO_x$—Pd/$SiO_2$ | 1273 | 63 | 1.3 | 95 | 3.0 | 0.2 | 0.1 | 0.3 | 0.0 | 0.0 | 0.0 | 0.0 | 98 |
| Ex. 6 | $CoO_x$—Pd/$SiO_2$ | 473 | 50 | 0.3 | 99 | 0.0 | 0.0 | 0.0 | 0.2 | 0.0 | 0.0 | 0.0 | 0.0 | 95 |
| Ex. 7 | $CoO_x$—Pd/$SiO_2$ | 573 | 63 | 0.7 | 99 | 0.1 | 0.0 | 0.0 | 0.2 | 0.0 | 0.0 | 0.1 | 0.0 | 102 |
| Ex. 8 | $CoO_x$—Pd/$SiO_2$ | 873 | 64 | 0.3 | 99 | 0.2 | 0.1 | 0.0 | 0.2 | 0.0 | 0.0 | 0.0 | 0.0 | 97 |
| Ex. 9 | $CoO_x$—Pd/$SiO_2$ | 873 | 60 | 0.0 | 99 | 0.2 | 0.2 | 0.0 | 0.6 | 0.0 | 0.0 | 0.0 | 0.0 | 96 |
| Ex. 10 | $CoO_x$—Pd/$SiO_2$ | 1173 | 63 | 0.0 | 99 | 0.2 | 0.2 | 0.0 | 0.5 | 0.0 | 0.0 | 0.1 | 0.0 | 99 |
| Com. Ex. 2 | $MoO_x$/$SiO_2$ | 1173 | 0.9 | — | — | — | — | — | — | — | — | — | — | 106 |
| Com. Ex. 3 | Pd/$SiO_2$ | 1173 | 0.6 | — | — | — | — | — | — | — | — | — | — | 106 |

BDO: 1,4-butanediol,
GBL: γ-butyrolactone,
THF: tetrahydrofuran,
BuA: butyric acid,
BuOH: 1-butanol,
PrA: propionic acid

[GC-FID (GC-2014)]
Column: HF-FFAP
Total analysis time: 30.00 min, inlet pressure: 87.6 kPa, column flow rate: 1.11 mL/min, linear velocity: 28.6 cm/s, split ratio: 25.0, total flow rate: 31.3 mL/min, injection mode: SPLIT, control mode: pressure, carrier gas: $N_2$, vaporization chamber temperature: 533 K, detector temperature: 533 K, filter signal time constant: 200 ms, number of sample cleaning: 5 times, number of sample injection: 2 times, sample injection amount: 0.5 μL, number of solvent cleaning: 3 times (both before and after), waiting time after sample inhalation: 0.2 s, waiting time after sample injection: 0.0 s, AOC power supply: on, column length: 30 m, column inner diameter: 0.250 mm column membrane thickness: 0.25 μm Temperature rising program of column: (initial) temperature 333 K, time 0.00 min, (one stage) rate: 10.00 K/rain, temperature 503 K, hold time 13.00 min
[GC-FID with Metanator (GC-2014)]
Column: Porapak-T
Time: 4.00 min, vaporization chamber temperature: 353 K, detector temperature: 353 K, frame: on, filter signal time constant: 200 ms, control mode: single L, detector signal input: CH1, background save: non, background correction: non, detector signal subtraction: non, signal attenuation: ×$2^{-4}$, kind of analog signal: wide, metanator temperature: 673 K As shown in Table 1, regarding the Mo—Pd catalyst, the conversion is remarkably improved in Examples 1 to 5 in which the reduction was conducted at higher temperature, as compared with Comparative Example 1 in which the reduction temperature is 473 K. Furthermore, the selectivity of γ-butyrolactone as an intermediate was large and the selectivity of tetrahydrofuran was small. Regarding the Co—Pd catalyst, according to Examples 6 to 10, by reducing at high temperature of 400 K or higher, high conversion rate was obtained, selectivity of γ-butyrolactone was large and the selectivity of tetrahydrofuran was small.

In Examples 1, 9 and 10, 1,4-butanediol is not formed. However, it is considered that in those examples, selectivity of γ-butyrolactone is high and γ-butyrolactone is converted to 1,4-butanediol by prolonging the reaction time of the hydrogenation reaction as is understood from the examples described after. Therefore, it is understood that the catalyst is useful as a catalyst for the production of 1,4-butanediol.

Examples 11 to 16

The hydrogenation reaction of succinic acid was conducted in the same manner as in Example 4, except that in Example 4, Mo—Pd catalyst reduced at 1173 K in a gas phase was used, and the reaction time of the hydrogenation reaction was changed to 12 hours in Example 11, 24 hours in Example 12, 48 hours in Example 13, 72 hours in Example 14, 96 hours in Example 16 and 120 hours in Example 16, as shown in Table 2 below, and each product was analyzed. The results including Example 4 are shown in Table 2.

Examples 17 to 21

The hydrogenation reaction of succinic acid was conducted in the same manner as in Example 7, except that in Example 7, Co—Pd catalyst reduced at 573 K in a gas phase was used, and the reaction time of the hydrogenation reaction was changed to 12 hours in Example 17, 24 hours in Example 18, 48 hours in Example 19, 72 hours in Example 20 and 96 hours in Example 21, as shown in Table 2 below, and each product was analyzed. The results including Example 7 are shown in Table 2.

tion reaction was about 20 hours or longer, and additionally, the selectivity of 1,4-butanediol could be remarkably increased. Furthermore, in the Co—Pd catalyst, the hydrogenation of from γ-butyrolactone to 1,4-butanediol is accelerated and dehydration of from 1,4-butanediol to tetrahydrofuran is slow. Therefore, the yield of 1,4-butanediol is increased by prolonging the reaction time, and the maximum yield was higher than the case of the Mo—Pd catalyst.

Examples 22 to 26

In Example 22, the hydrogenation reaction of succinic acid was conducted in the same manner as in Example 7,

TABLE 2

| | Catalyst | Reaction Time (h) | Conversion rate (%) | Selectivity (%) | | | | | | | | | | Mass Balance (%) |
| --- | --- | --- | --- | --- | --- | --- | --- | --- | --- | --- | --- | --- | --- | --- |
| | | | | BDO | GBL | THF | BuA | BuOH | PrA | CO | $CO_2$ | $CH_4$ | $C_2H_6$ | |
| Ex. 4 | $MoO_x$—Pd/$SiO_2$ | 4 | 65 | 3.2 | 95 | 1.5 | 0.1 | 0.1 | 0.1 | 0.0 | 0.0 | 0.0 | 0.0 | 96 |
| Ex. 11 | $MoO_x$—Pd/$SiO_2$ | 12 | 89 | 6.7 | 85 | 7.4 | 0.3 | 0.1 | 0.0 | 0.0 | 0.0 | 0.1 | 0.0 | 100 |
| Ex. 12 | $MoO_x$—Pd/$SiO_2$ | 24 | >99 | 46 | 45 | 7.7 | 0.5 | 0.8 | 0.0 | 0.0 | 0.0 | 0.0 | 0.0 | 94 |
| Ex. 13 | $MoO_x$—Pd/$SiO_2$ | 48 | >99 | 55 | 30 | 12 | 0.9 | 2.0 | 0.0 | 0.0 | 0.0 | 0.0 | 0.0 | 95 |
| Ex. 14 | $MoO_x$—Pd/$SiO_2$ | 72 | >99 | 40 | 19 | 37 | 0.8 | 3.5 | 0.0 | 0.0 | 0.0 | 0.0 | 0.1 | 95 |
| Ex. 15 | $MoO_x$—Pd/$SiO_2$ | 96 | >99 | 31 | 9.0 | 56 | 0.2 | 4.0 | 0.0 | 0.0 | 0.0 | 0.0 | 0.0 | 94 |
| Ex. 16 | $MoO_x$—Pd/$SiO_2$ | 120 | >99 | 4.5 | 0.7 | 90 | 0.1 | 4.6 | 0.0 | 0.0 | 0.0 | 0.0 | 0.0 | 96 |
| Ex. 7 | $CoO_x$—Pd/$SiO_2$ | 4 | 63 | 0.7 | 99 | 0.1 | 0.0 | 0.0 | 0.2 | 0.0 | 0.0 | 0.1 | 0.0 | 102 |
| Ex. 17 | $CoO_x$—Pd/$SiO_2$ | 12 | 93 | 0.9 | 99 | 0.2 | 0.0 | 0.0 | 0.3 | 0.0 | 0.5 | 0.0 | 0.0 | 100 |
| Ex. 18 | $CoO_x$—Pd/$SiO_2$ | 24 | >99 | 66 | 31 | 0.7 | 0.1 | 1.0 | 0.0 | 0.0 | 0.0 | 0.5 | 0.1 | 95 |
| Ex. 19 | $CoO_x$—Pd/$SiO_2$ | 48 | >99 | 75 | 20 | 2.3 | 0.1 | 1.3 | 0.0 | 0.0 | 0.0 | 0.4 | 6.1 | 97 |
| Ex. 20 | $CoO_x$—Pd/$SiO_2$ | 72 | 98 | 86 | 7.1 | 3.6 | 0.2 | 2.8 | 0.5 | 0.0 | 0.0 | 0.0 | 0.0 | 94 |
| Ex. 21 | $CoO_x$—Pd/$SiO_2$ | 96 | >99 | 81 | 5.5 | 9.4 | 0.1 | 3.2 | 0.5 | 0.0 | 0.0 | 0.0 | 0.0 | 99 |

BDO: 1,4-butanediol,
GBL: γ-butyrolactone,
THF: tetrahydrofuran,
BuA: butyric acid,
BuOH: 1-butanol,
PrA: propionic acid As shown in Table 2, the selectivity of 1,4-butanediol could be increased by prolonging the reaction time of the hydrogenation reaction. As shown in Examples 4 and 11 to 16, in the Mo—Pd catalyst, the conversion could be about 100% by that the reaction time of the hydrogenation reaction was about 20 hours or longer, and additionally, the selectivity of 1,4-butanediol could be remarkably increased by that the reaction time was about 20 to 100 hours, and furthermore, about 20 to 80 tours. As shown in Examples 7 and 17 to 21, in the Co—Pd catalyst, the conversion could be about 100% by that the reaction time of the hydrogenaexcept that in Example 7, Co—Pd catalyst (Co/Pd (molar ratio)=20) reduced at 573 K in a gas phase was used and the reaction time of the hydrogenation reaction was changed to 2 hours, and the product, was analyzed. In Examples 23 to 26, gas phase reduction was conducted at 573 K for 1 hour in the same manner as in Example 7 using the Co—Pd catalyst (Co/Pd (molar ratio)=8, 12, 16 and 32) obtained in Production Example 5. Thereafter, the hydrogenation reaction was conducted for 2 hours in the same manner as in Example 22, and the products obtained were analyzed. The results are shown in Table 3.

TABLE 3

| | Catalyst | Co/Pd | Conversion rate (%) | Selectivity (%) | | | | | | | | | | Mass Balance (%) |
| --- | --- | --- | --- | --- | --- | --- | --- | --- | --- | --- | --- | --- | --- | --- |
| | | | | BDO | GBL | THF | BuA | BuOH | PrA | CO | $CO_2$ | $CH_4$ | $C_2H_6$ | |
| Ex. 23 | $CoO_x$—Pd/$SiO_2$ | 8 | 24 | 0.9 | 99 | 0.2 | 0.0 | 0.1 | 0.3 | 0.1 | 0.0 | 0.0 | 0.0 | 101 |
| Ex. 24 | $CoO_x$—Pd/$SiO_2$ | 12 | 35 | 0.0 | 99 | 0.2 | 0.0 | 0.1 | 0.3 | 0.0 | 0.0 | 0.0 | 0.0 | 99 |
| Ex. 25 | $CoO_x$—Pd/$SiO_2$ | 16 | 36 | 0.1 | 99 | 0.1 | 0.0 | 0.1 | 0.2 | 0.0 | 0.1 | 0.1 | 0.0 | 99 |
| Ex. 22 | $CoO_x$—Pd/$SiO_2$ | 20 | 39 | 0.1 | 99 | 0.3 | 0.2 | 0.0 | 0.3 | 0.0 | 0.0 | 0.1 | 0.1 | 101 |
| Ex. 26 | $CoO_x$—Pd/$SiO_2$ | 32 | 46 | 0.4 | 99 | 0.1 | 0.0 | 0.1 | 0.2 | 0.0 | 0.0 | 0.1 | 0.0 | 99 |

BDO: 1,4-butanediol,
GBL: γ-butyrolactone,
THF: tetrahydrofuran,
BuA: butyric acid,
BuOH: 1-butanol,
PrA: propionic acid As shown in Table 3, in the Co—Pd catalyst, the activity in succinic acid hydrogenation and the yield of 1,4-butanediol were improved in association with the increase of the amount of Co supported, in a range of Co/Pd molar ratio of 8 to 32, and the activity was maximum in Co/Pd=32. In Examples 22 to 26, the amount of 1,4-butanediol formed is small, but the selectivity of γ-butyrolactone is high, and it is considered that γ-butyrolactone is converted to 1,4-butanediol by prolonging the reaction time of the hydrogenation reaction. Therefore, it is understood that the catalysts are useful as a catalyst for production of 1,4-butanediol.

Although some embodiments of the present invention have been described above, those embodiments are exemplified as an example, and do not intend to limit the scope of the present invention. Those embodiments can be carried out in other various forms, and various omissions, replacements and changes can be made without departing the gist of the present, invention. Those embodiments and their omissions, replacements and changes are included in the scope and gist of the present invention and also in the invention described in the claim and its equivalent scope.

The invention claimed is:

1. A production method of a catalyst for hydrogenation for hydrogenating at least one of dicarboxylic acid or its acid anhydride, comprising:
   supporting at least one of palladium or platinum, and cobalt, as a metal component, on a carrier, and
   subjecting the resulting carrier to a reduction treatment at 400 K or higher,
   wherein a whole part of the metal component consists of: (i) the at least one of palladium or platinum and/or a compound of the at least one of palladium or platinum and (ii) the cobalt and/or a compound of the cobalt.

2. The production method of a catalyst for hydrogenation according to claim 1, wherein the reduction treatment is a reduction treatment in a gas phase.

3. The production method of a catalyst for hydrogenation according to claim 1, wherein the catalyst contains the at least one of palladium or platinum in a form of a simple substance, and the cobalt in a form of a simple substance and/or an oxide.

4. A production method of a catalyst for hydrogenation for hydrogenating at least one of dicarboxylic acid or its acid anhydride, comprising:
   supporting at least one of palladium or platinum, and molybdenum, as a metal component, on a carrier, and
   subjecting the resulting carrier to a reduction treatment at 1000K or higher,
   wherein a whole part of the metal component consists of: (i) the at least one of palladium or platinum and/or a compound of the at least one of palladium or platinum and (ii) the molybdenum and/or a compound of the molybdenum.

5. The production method of a catalyst for hydrogenation according to claim 4, wherein the reduction treatment is a reduction treatment in a gas phase.

6. The production method of a catalyst for hydrogenation according to claim 4, wherein the catalyst contains the at least one of palladium or platinum in a form of a simple substance, and the molybdenum in a form of a simple substance and/or an oxide.

7. A production method of a diol, comprising:
   subjecting a carrier having supported thereon at least one of palladium or platinum, and cobalt, as a metal component, to a reduction treatment at 400 K or higher, wherein a whole part of the metal component consists of: (i) the at least one of palladium or platinum and/or a compound of the at least one of palladium or platinum; and (ii) the cobalt and/or a compound of the cobalt, and
   hydrogenating at least one of dicarboxylic acid or its acid anhydride in the presence of the reduced carrier as a catalyst, thereby producing a diol.

8. The production method of a diol according to claim 7, wherein the reduction treatment is a reduction treatment in a gas phase.

9. The production method of a diol according to claim 7, wherein the catalyst contains the at least one of palladium or platinum in a form of a simple substance, and the cobalt in a form of a simple substance and/or an oxide.

10. A production method of a diol, comprising:
    subjecting a carrier having supported thereon at least one of palladium or platinum, and molybdenum, as a metal component, to a reduction treatment at 1000K or higher, wherein a whole part of the metal component consists of: (i) the at least one of palladium or platinum and/or a compound of the at least one of palladium or platinum; and (ii) the molybdenum and/or a compound of the molybdenum, and
    hydrogenating at least one of dicarboxylic acid or its acid anhydride in the presence of the reduced carrier as a catalyst, thereby producing a diol.

11. The production method of a diol according to claim 10, wherein the reduction treatment is a reduction treatment in a gas phase.

12. The production method of a diol according to claim 10, wherein the catalyst contains the at least one of palladium or platinum in a form of a simple substance, and the molybdenum in a form of a simple substance and/or an oxide.

13. A catalyst for hydrogenation for hydrogenating at least one of dicarboxylic acid or its acid anhydride, which comprises a carrier, at least one of palladium or platinum supported on the carrier, and cobalt supported on the carrier, and is obtained by subjecting the resulting carrier to a reduction treatment at 400 K or higher, wherein a whole part of a metal component supported on the carrier consists of: (i) the at least one of palladium or platinum and/or a compound of the at least one of palladium or platinum; and (ii) the cobalt and/or a compound of the cobalt.

14. The catalyst for hydrogenation according to claim 13, wherein the at least one of palladium or platinum is contained in a form of a simple substance, and the cobalt is contained in a form of a simple substance and/or an oxide.

15. A catalyst for hydrogenation for hydrogenating at least one of dicarboxylic acid or its acid anhydride, which comprises a carrier, at least one of palladium or platinum supported on the carrier, and molybdenum supported on the carrier, and is obtained by subjecting the resulting carrier to a reduction treatment at 1000K or higher, wherein a whole part of a metal component supported on the carrier consists of: (i) the at least one of palladium or platinum and/or a compound of the at least one of palladium or platinum and (ii) the molybdenum and/or a compound of the molybdenum.

16. The catalyst for hydrogenation according to claim 15, wherein the at least one of palladium or platinum is contained in a form of a simple substance, and the molybdenum is contained in a form of a simple substance and/or an oxide.

* * * * *